United States Patent [19]

Poler

[11] 4,122,556

[45] Oct. 31, 1978

[54] INTRA-OCULAR LENS

[76] Inventor: Stanley Poler, 78 E. Second St., New York, N.Y. 10003

[21] Appl. No.: 780,445

[22] Filed: Mar. 23, 1977

[51] Int. Cl.$^2$ .......................... A61F 1/16; A61F 1/24
[52] U.S. Cl. ........................................ 3/13; 128/221; 128/303 R; 206/438; 206/571; 206/572
[58] Field of Search ................. 3/13; 128/218 N, 221, 128/303 R; 206/438, 570, 571, 572

[56] References Cited

U.S. PATENT DOCUMENTS

| | | | |
|---|---|---|---|
| 1,625,035 | 4/1927 | Lilly | 206/571 |
| 2,716,983 | 9/1955 | Windischman et al. | 128/221 |
| 3,013,656 | 12/1961 | Murphy, Jr. | 206/572 |
| 3,076,457 | 2/1963 | Copen | 128/221 |
| 3,920,001 | 11/1975 | Edwards | 128/221 X |
| 3,925,825 | 12/1975 | Richards et al. | 3/13 |
| 4,056,855 | 11/1977 | Kelman | 3/13 |

OTHER PUBLICATIONS

"Artiphakia & Anieseikonia", by R. C. Troutman, American Journal of Ophthalmology, vol. 56, No. 2, Oct. 1963, pp. 630–633.

*Primary Examiner*—Ronald L. Frinks
*Attorney, Agent, or Firm*—Hopgood, Calimafde, Kalil, Blaustein & Lieberman

[57] ABSTRACT

The invention contemplates improved techniques for making lens implants for use in ophthalmological surgery, the lens being a replacement for a cataract-clouded natural lens, and the replacement being installed in the pupil at the iris as the operative step following removal of the cataracted lens. The lens produced by the inventive method features adapter structure assembled to an intra-ocular lens element and having first and second pluralities of radially outward stabilizing feet, the feet of one plurality being in angularly spaced and interlaced relation with the feet of the other plurality; and the respective pluralities of stabilizing feet are on opposite sides of the iris, enabling the iris to retain and position the implanted lens. At least two diametrically opposed feet are resiliently compliant and have openings for removable engagement with a manipulative tool.

32 Claims, 12 Drawing Figures

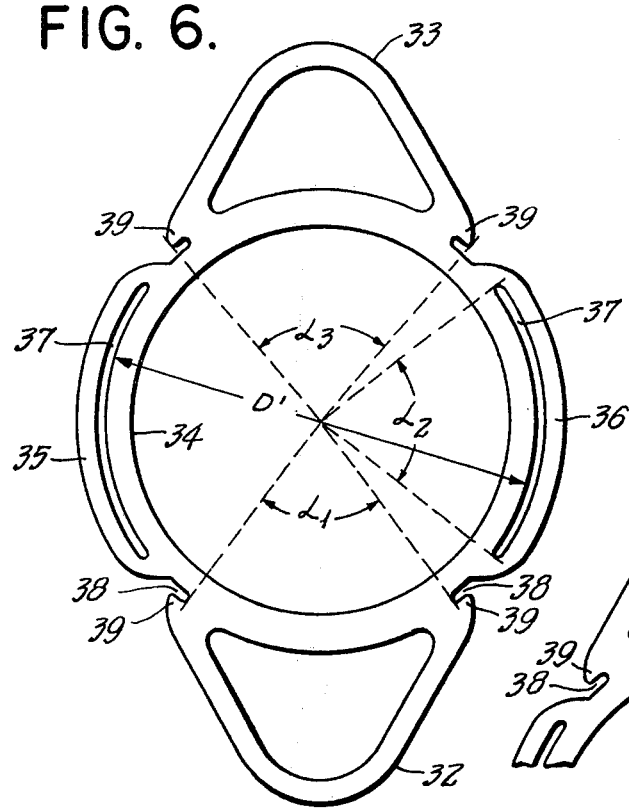
FIG. 6.
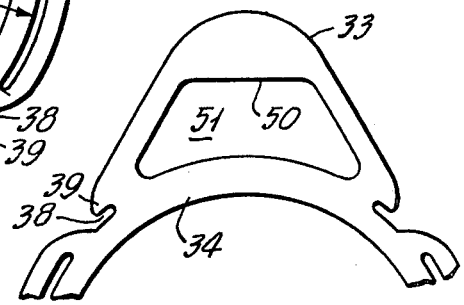
FIG. 11.
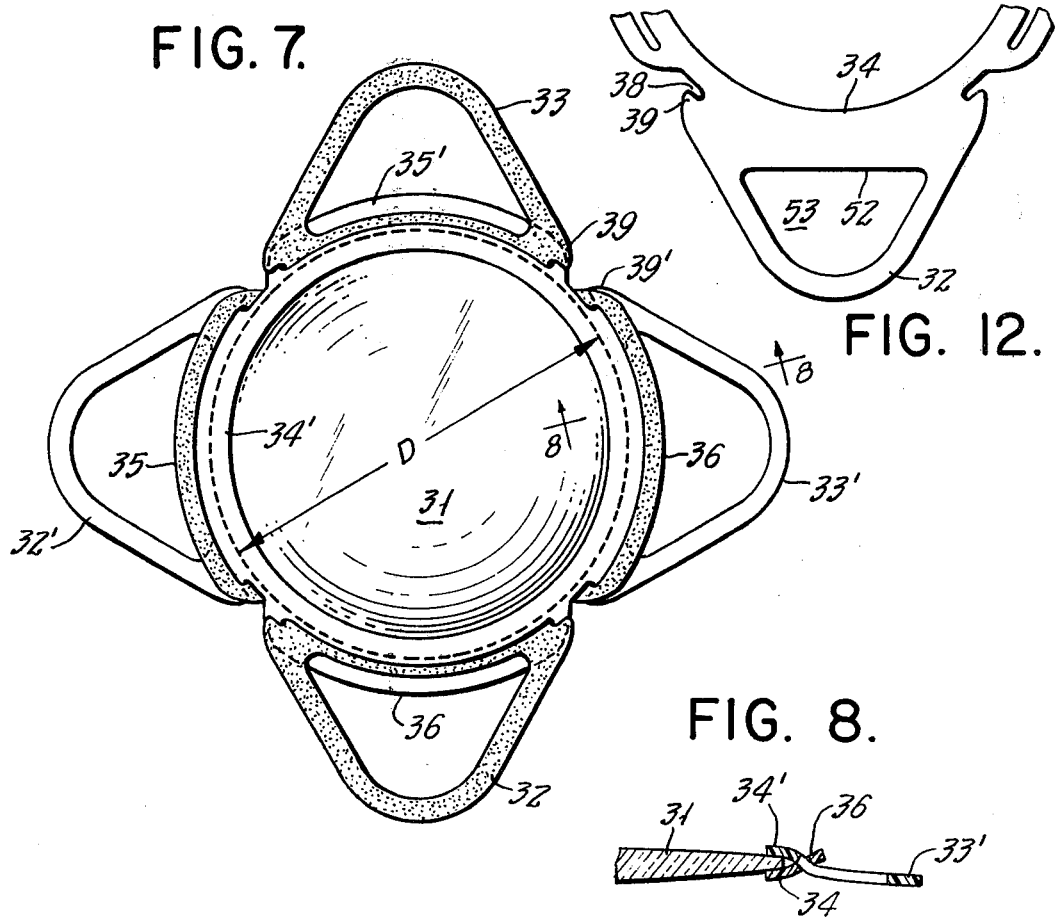
FIG. 7.
FIG. 12.
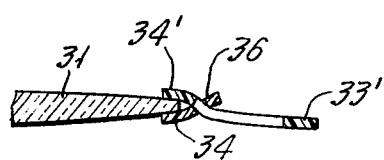
FIG. 8.

INTRA-OCULAR LENS

This invention relates to structures for making an improved lens implant, as a replacement for a cataract-clouded or otherwise diseased natural lens. The invention represents improvement over structures described in my copending application, Ser. No. 691,033, filed May 28, 1976, now U.S. Pat. No. 4,073,014 and it employs techniques of manufacture described in my copending application Ser. No. 780,682 filed on even date herewith and now U.S. Pat. No. 4,080,709. Reference is therefore made to said applications for greater background detail as to structures and as to manufacturing technique.

Regardless of the structure of an intra-ocular lens and its mount, relatively great surgical skill is required for installation at an iris opening, if post-operative trauma is to be avoided.

It is an object of the present invention to provide improved mounting structure for an intra-ocular lens.

Another object is to provide such structure lending itself to simplified iris-stabilized installation.

A specific object is to meet the above objects with a pre-assembled lens and mount which can be operatively manipulated and installed at the end of a hypodermic needle.

Another specific object is to provide an intra-ocular lens and mount with improved tool-manipulable resiliently compliant lens-positioning feet which will automatically spring into permanent engagement with the inner side of the iris, upon tool removal.

Still another specific object is to meet the above objects with coacting lens-mount and tool structure whereby eye-filling saline solution may be introduced as the tool structure is being inserted or removed.

It is a general object to meet the above objects with a pre-assembled lens and mount and manipulative tool so as to permit safe and reliable operative installation to an iris opening with substantially less requirement for operative skill and with inherently greater assurance of trauma-free post-operative results.

Other objects and various further features of novelty and invention will be pointed out or will occur to others skilled in the art from a reading of the following specification in conjunction with the accompanying drawings. In said drawings, which show, for illustrative purposes only, preferred forms of the invention:

FIG. 6 is a plan view of an undeformed blank for part of the mounting adapter of FIG. 5;

FIG. 7 is a view similar to FIG. 6, to show two blanks of FIG. 6 in assembly to each other and to the lens;

FIG. 8 is a sectional view of the parts of FIG. 7 in pre-assembled relation to the intra-ocular lens, the section being taken at 8—8 in FIG. 7;

FIGS. 11 and 12 are similar fragmentary views of modifications of the blank of FIG. 6.

Figure 1:
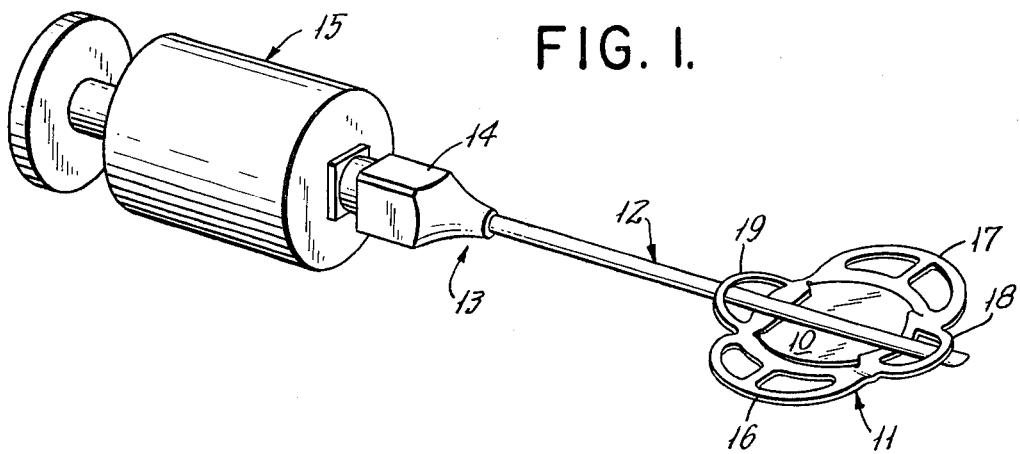
FIG. 1 is an enlarged view in perspective of a preassembled intra-ocular lens and mount, the same being pre-assembled to a manipulative tool.

In FIG. 1, an intra-ocular lens 10, which may be of suitable injection-molded plastic but which is preferably of finish-ground optical glass, is assembled to a single-piece mounting adapter 11, and the latter is removably assembled to the elongate end 12 of manipulative-tool means 13. The tool means 13 will be recognized as essentially a hypodermic needle which may be disposable and which includes at its base end a fitting 14 for removable application to a syringe 15. The mounting adapter 11 may be formed from a thin sheet of resiliently compliant material by techniques described in said copending applications and as shown comprises a first and larger pair of radially outward iris-stabilizing lens-positioning feet 16–17 at first opposed quadrant locations, and a second and smaller pair of radially outward iris-stabilizing lens-positioning feet 18–19 at the remaining opposed quadrant locations. The smaller feet 18–19 are for insertion via an iris opening and are shown to be apertured and to have been resiliently bent to one axial side of the lens-and-mount assembly, being thus retained by passage of the needle end 12 through the then-diametrically aligned openings of feet 18. It will be understood that upon longitudinal retraction of needle 12 from its engagement with the apertures of feet 18–19, the latter will naturally spring back to their normally more flat or radially outward orientation.

Figure 2:
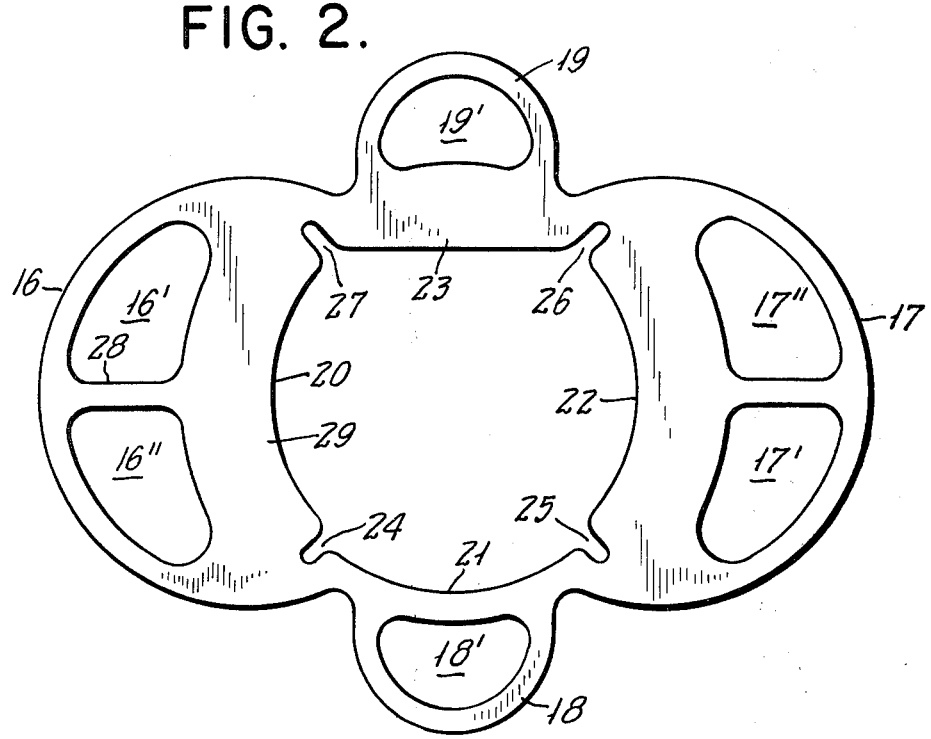
FIG. 2 is a plan view of an undeformed blank for the mounting adapter of the pre-assembled lens and mount of FIG. 1.
Figure 3:
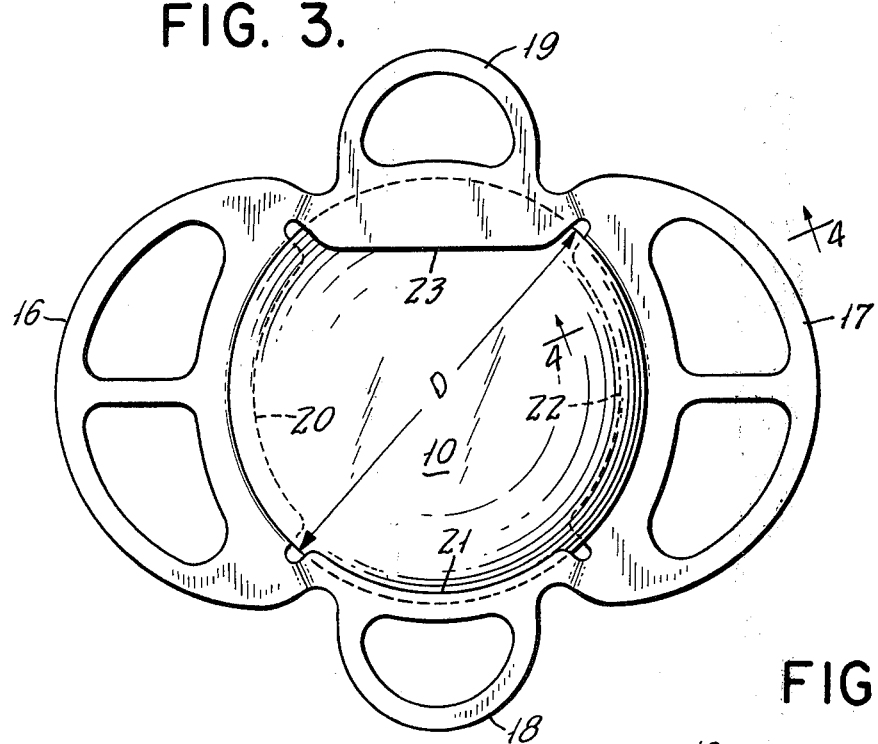
FIG. 3 is a view similar to FIG. 2, after deformation and assembly to the intra-ocular lens.
Figure 4:
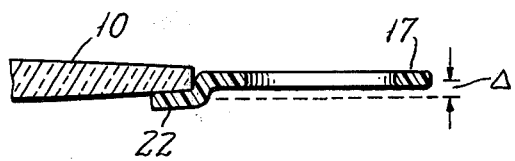
FIG. 4 is a sectional view taken at 4—4 in FIG. 3.

Turning now more particularly to FIGS. 2 to 4, the mounting adapter 11 is seen to have been initially characterized by the blank outlines of FIG. 2, being thus cut-out from sheet material by one of the photo-etch or other techniques described in said applications, and being thereafter of the appearance shown in FIG. 3 when assembled to the lens element 10. The blank of FIG. 2 comprises a circumferentially continuous centrally open body characterized for substantial conformance with and generally registering adjacency to the periphery of lens element 10, the latter being circular as shown in FIG. 3. This body is essentially a series of four integrally connected angularly spaced quadrant tabs or segments 20-21-22-23, separated by cutaway regions or slots 24-25-26-27. All tabs or segments 20-21-22-23 extend radially inward of the peripheral diameter D of lens 10 for axial-end engagement therewith, and the cutaway regions or slots 24-25-26-27 extend radially outward to at least the diameter D and preferably slightly beyond said diameter, as shown in FIG. 3. The segment 23 may be of greater radial width than its diametrically opposite counterpart 21, to permit inscription of serial number and/or lens-identifying data thereon.

The pairs 16–17 and 18–19 of iris-stabilizing feet are integral with the adapter body at the respective quadrant regions of tabs 20 to 23. For the smaller feet 18–19, the provision of tool accommodating apertures 18'–19' limits these feet essentially to outwardly bowed strips which are integrally united to segments 21-23 at angularly spaced locations, near slots 24–25 in the case of foot 18, and near slots 26–27 in the case of foot 19; such a structural relation will be understood to characterize feet 18–19 with relatively great flexible compliance for the bending needed for the tool-engagement and implant manipulation, while assuring resilient restoration to substantially radial-plane orientation upon release from tool 13. For the larger feet 16–17, a substantial economy of weight is achieved by providing apertures 16'–16" and 17'–17" which reduce these feet to essentially the bowed integral-strip nature described for feet 18–19. The openings 16'–16" and 17'–17" are separated by radius-stabilizing strips as at 28, and these openings may (as with openings 18'–19') extend radially inward to substantially the locus of the lens periphery; however, as shown, a more stiff (i.e., less flexible) integrity of feet 16–17 is assured by a greater mass of body area at segments 20–22.

It has been noted that each quadrant of the mount of FIGS. 1 to 4 is identified with a lens-engaging tab or segment and with an associated iris-stabilizing foot — for example, the diametrically opposite larger feet 16–17 and their associated tabs 20–22 and, in angularly interlaced relation therewith, the diametrically opposite smaller feet 18–19 and their associated tabs 21–23. Fully stabilized positioning and retention of an assembled lens 10 may be realized by placing the blank over the lens, and by then resiliently bending feet 16–17 downwardly, i.e., axially away from lens 10. Such bending for the case of foot 16 will be seen to elevate tab 20 past a position of snap engagement over the adjacent peripheral region of lens 10, and the same is true, in the diametrically opposite sense, for the case of tab 22 on foot 17; subsequent release of the feet 16–17 allows feet 16–17 to spring radially outwardly, so that lens 10 is thereafter held by an axial preload via tabs 20–22 in opposition to a similar preload via tabs 21–23. Such interlaced-quadrant engagement of opposite sides of lens 10 is shown by successive dashed and solid lines of the lens periphery of FIG. 3, and it will be appreciated that in the process of establishing such axially preloaded assembly to lens 10, the feet 16–17 of one plurality are necessarily axially displaced in relation to the feet 18–19 of the other plurality, thereby providing a natural adaptation of feet 16–17 to the anterior side of the iris and of feet 18–19 to the posterior side.

While lens retention and assembly to the adapter mount of FIGS. 1 to 4 may be merely by simple assembly to the flat blank of FIG. 2, it is my preference that certain permanent bends be applied to the blank of FIG. 2 prior to lens assembly. The bends establish an axial offset $\Delta$ (see FIG. 4) as between a first radial plane of segments 20–22, on the one hand, and a second radial plane of feet 16–17, on the other hand. The extent of this axial offset is preferably just short of the axial thickness of lens 10 at its engaged periphery, and this offset is essentially localized at the body regions adjacent the tab-separating slots 24–25–26–27. The net result of bending to the offset $\Delta$ accounts for slight radially inward displacement of the larger feet 17, as is apparent from comparison of FIG. 3 with FIG. 2.

In the embodiment of FIGS. 5 to 8, the mounting adapter 30 for an intra-ocular lens 31 is an assembled interconnection of two halves, which may be duplicates of each other, utilizing the blank configuration of FIG. 6. As with already described structure, the embodiment of FIGS. 5 to 8 provides two apertured resiliently compliant feet 32–33 at diametrically opposed locations, for subassembly to the elongate end 12 of a manipulative tool 13. The two opposed feet 32–33 are integral formations of one of the two halves of adapter 30; the similar opposed-foot formations of the other half are identified 32'–33', and I shall continue to employ primed notation to enable differentiation between corresponding parts of one as distinguished from the other of the two assembled half elements of the mounting adapter 30.

Referring more particularly to FIG. 6, each element of the mounting adapter 30 is seen to be initially characterized by a blank of resiliently compliant sheet material, photo-etched or otherwise cut as described in said application. The blank of FIG. 6 comprises a circumferentially continuous centrally open body 34 with a circular inner edge of diameter less than the diameter D of the periphery of lens 31. The body 34 is of substantially uniform radial extent throughout and has an outer diameter D' which is substantially that of the lens 31. The apertured feet 32–33 comprise essentially outwardly bowed strips which are integrally connected at their ends to the body 34, each within its own quadrant region about a central axis. In the remaining quadrant regions, foot-engaging strips 35–36 are outwardly bowed and integrally connected at their ends to the body 34, being slightly radially offset from the adjacent segment of body 34 and defining an arcuate slot (37) therebetween. The bowed strips of feet 32–33 are locally recessed, as at 38, to define retaining detent projections 39, and the effective angular span $\alpha 1$ between recesses 38 of one foot (32, 33) is less than the effective angular span $\alpha 2$ between limits of each arcuate slot 37, while the effective angular span $\alpha 3$ subtended by detents 39 exceeds the slot span $\alpha 2$.

Referring to FIG. 7, assembly of the two elements of adapter 30 is made by orienting the feet 32–33 of one part in quadrant interlace with the feet 32'–33' of the other part. The feet 32–33 of one part are inserted through the arcuate slots 37' of the other part, and the feet 32'–33' of the other part are inserted through the arcuate slots 37 of the one part, with lens 31 interposed between bodies 34–34'; the insertions are pressed to the point of snap-lock retention at detents 38–38' at limits of the arcuate slots 37'–37. At conclusion of such snap-locked assembly, the foot-engaging strips 35–36 (35'–36') engage over and retain the inserted feet 32'–33' (32–33) and apply lens-retaining axial preload forces at the lens periphery, thereby causing a first pair of opposed feet 32–33 to be in axially offset relation with the other pair of opposed feet 32'–33'. It will be appreciated that in ultimate implanted assembly to an iris opening, these separate pairs of offset feet engage the respective anterior and posterior sides of the iris.

Figure 9:
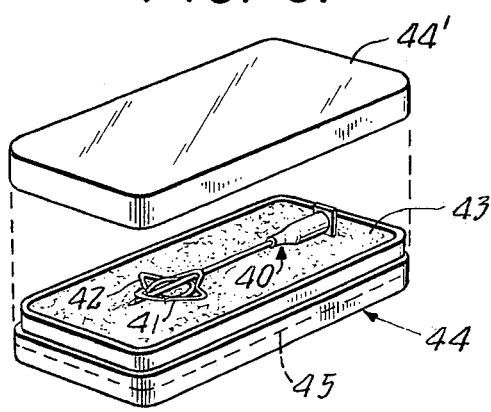
FIG. 9 is a perspective view of a kit package for use in effecting surgical implantation of an intra-ocular lens.

FIG. 9 illustrates an intra-ocular lens-implant kit of maximum convenience to the ophthalmic surgeon. The needle-tool element 40 and an assembled lens 41 and lens mount 42 are included in this kit, being shown pre-assembled to the needle-tool element 40 in readiness for removable attachment to a syringe, e.g., syringe 15. The parts 40–41–42 are shown on a shock-mounting sterile bed or cushion 43, as of urethane or the like foam, within the base of a disposable plastic case 44. Case 44 is closed by a removable clear-plastic cover 44' which normally holds the parts 40–41–42 in slight compression against the bed 43, and a dashed line 45 will be understood to be suggestive of a peripherally continuous rip strip by which the contents of a sealed and sterile package 44 can have once-only access.

Figure 10:
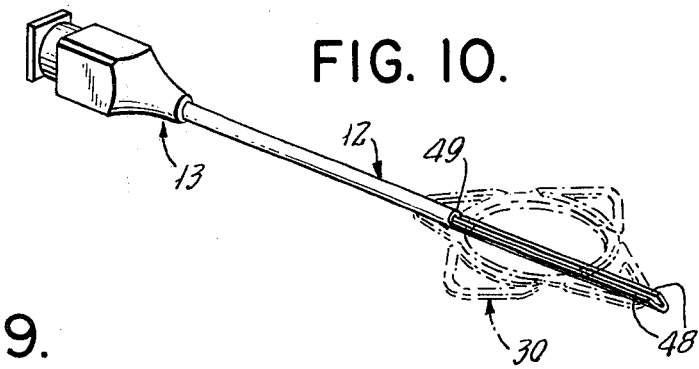
FIG. 10 is a fragmentary view in perspective to show the lens-mount engaging underside portion of the manipulative tool of FIGS. 1 and 5.

FIG. 10 provides illustration of detail by means of which the needle end 12 can more usefully serve lens and lens-mount manipulation. At slightly greater than the longitudinal extent required to engage the two apertured legs 18–19 (or 32–33), the end 12 is longitudinally truncated, at 48, as along a diametral plane of the needle axis, to a radial shoulder or other stop means 49. Such truncation will be understood to provide a degree of key-engagement with adjacent adapter-mount body material, thereby providing resistance against lens-mount rotation about the needle itself. And the shoulder 49 of such truncation will be understood to axially interfere with adjacent body material of the mount, thus enabling a safe measure of axially inward manipulative thrust, without having the needle end cause damage within the posterior cavity of the eye.

FIGS. 11 and 12 illustrate slight modifications of the blank of FIG. 6 whereby manipulative effectiveness may be enhanced when used with a tool as at 13, and whereby at the same time an extended surface area is provided for inscription of serial number or other identification of the lens thereby mounted. In both cases, the extended area is provided by a chordlike edge formation in the contour of the tool-insertion opening defined by one of the outwardly bowed strips 32–33. In FIG. 11, the chordlike edge 50 spans the tool-insertion opening 51 at bowed strip 33, and in FIG. 12, the chordlike edge 52 spans the tool-insertion opening 53 at bowed strip 32. In either of these cases, a keyed engagement results between key formations 48 of tool 13 at the chordlike edge (50 or 52), provided that the needle is initially correctly assembled, and the stop or shoulder formation 49 performs the axial-insertion limitation already described.

Figure 5:
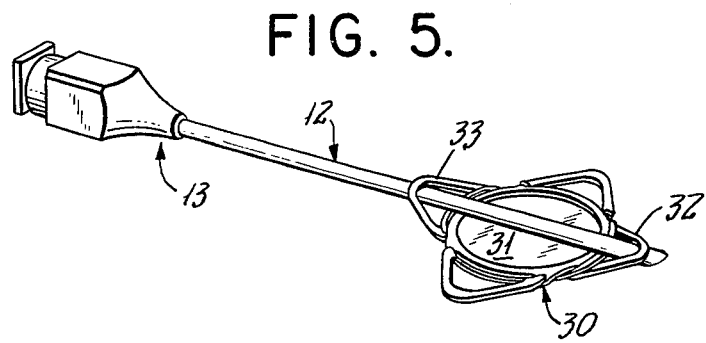
FIG. 5 is a view similar to FIG. 1, to illustrate a different mounting-adapter in pre-assembly to the intra-ocular lens.

In a typical employment of either of the general configurations of FIGS. 1 or 5, a syringe 15 loaded with saline solution is fitted to the pre-assembled tool 13 and lens and lens-mount assembly. After the customary corneal incision and removal or other disposition of the cataracted lens, the tool 13–15 is manipulated to place both of the resiliently bent feet 18–19 (32–33) behind the iris opening, retaining the remaining feet 16–17 (32′–33′) in front of the iris opening. Frictional engagement of the implant with the iris may be relied upon to drag the implant as the needle end 12 is withdrawn, and the plunger of the syringe 15 may be actuated throughout the manipulative process so as to flush and fill the eye cavity with saline solution, thereby avoiding the need for a separate filling operation once the needle has been withdrawn. Of course, as the needle is withdrawn from each foot-aperture engagement, the applicable foot is released for iris-stabilizing action, against the posterior side of the iris. The needle is discarded and surgery is then completed according to customary cataract-removal procedures.

The described invention will be seen to have achieved all stated objects with structure which not only can be economically produced in substantial quantity and with great precision but which can also be constructed to such inherent lightness of weight as to enable use of the finest-finished optical-glass lenses, ground to prescription, if so required. This, of course, means greatest comfort and least danger of post-operative trauma for the patient. And the adaptability to a manipulative tool (with the moving parts) which can also provide for saline-solution injection means such a simplification of operative procedures as to permit lens-implant surgery within the manipulative-skill capabilities of vastly expanded numbers of ophthalmic technicians. Furthermore, particularly for the case of the lens-mount configuration of FIGS. 5 and 7, full and continuous circumferential overlap is provided to protect against any edge contact of a glass lens element with eye tissue, and to a limited but effective extent such protection is also afforded with the embodiment of FIGS. 1 and 3.

While the invention has been described in detail for the preferred forms shown, it will be understood that modifications may be made without departing from the scope of the invention. For example, the reference herein to a syringe will be understood to be but illustrative of, and therefore generically to describe, a manually controllable means for injecting saline solution and when needed or useful during surgery; in other words, a disposable squeeze bottle with packaged saline solution and adaptable to or embodying a disposable tool 13 may be perfect for many surgical situations and is to be understood to be within the meaning of the word "syringe" as used herein. Also, the described procedure involving tool-manipulated insertion of the intra-ocular lens and its mount may not be the procedure ultimately to be preferred for tool-insertion; for example, by using the syringe to fill and effectively float all or most of the cornea and other internal parts of the eye, it may prove most desirable to keep the needle end 12 at all times on the anterior side of the iris, relying upon manipulation of the lens-and-mount subassembly to transiently deflect iris tissue for insertion of feet 16–17 (32′–33′) into the posterior region, in which case utmost protection is afforded against undue flexure of the cornea and against tool contact with any tissue.

What is claimed is:

1. As an article of manufacture, an optically finished intra-ocular lens element having a generally circular periphery about its optical axis, and a mounting adapter for said lens element, said adapter comprising circumferentially continuous ring-body means is substantial conformance with and in generally registering adjacency to the periphery of said lens element, said body means including (a) first retaining means engaging said lens element at least at diametrically opposed locations and in retaining overlap over one axial side of said periphery and (b) second retaining means engaging said lens element at least at diametrically opposed locations which are angularly interlaced with said first-mentioned locations and which are in retaining overlap over the other axial side of said periphery, and first and second pluralities of lens-positioning feet integral with said ring body and radially outwardly extending therefrom in angularly spaced and interlaced relation, the feet of at least one of said pairs being flexibly compliant to permit transient resilient inward bending to facilitate operative insertion via an iris opening.

2. The article of claim 1, in which each of the feet of said one pair of feet is a radially outwardly bowed strip integrally formed at its ends with angularly spaced regions of said body means, thereby defining an opening between each strip and the angularly adjacent portion of said lens element whereby an elongate manipulative tool may pass through the two generally diametrically aligned such openings defined by said one pair of feet.

3. The article of claim 1, in which said ring-body means is a single piece of resiliently compliant material.

4. The article of claim 3, in which said first retaining means and said second retaining means respectively comprise first and second pairs of retaining members, and in which each member is an arcuate length spanning its axial side of said lens element for an angular extent which is substantially within a separate quadrant of said periphery.

5. The article of claim 4, in which at least one of said retaining members is of greater radial width than others of said retaining members, whereby manufacturing data such as serial number may be inscribed thereon.

6. The article of claim 1, in which said ring-body means comprises two ring-body members of resiliently compliant material, each ring-body member having a circumferentially continuous inner-rim formation of less than the outer diameter of said lens element and in axial-retaining abutment with a different one of the axial ends of said lens element, said first pair of lens-positioning feet being integrally formed with one of said ring-body members and said second pair of lens-positioning feet being integrally formed with the other of said ring-body members, and foot-engaging means integrally formed with each of said ring-body members in angular interlace with the lens-positioning feet thereof and having interlocking engagement with one of the lens-positioning feet of the other ring-body member when the lens-positioning feet of one ring-body member are in angularly interlaced relation with the lens-positioning feet of the other ring-body member.

7. The article of claim 6, in which each said foot-engaging means comprises an arcuate tab having a foot-receiving locating slot at a radius which is at least as great as the outer radius of said lens element.

8. The article of claim 6, in which each lens-positioning foot is integrally formed with the adjacent portion of its inner-rim formation over an effective angular span which is a substantial fraction of a quadrant of its associated inner-rim formation.

9. The article of claim 7, in which each locating slot is arcuate and of an effective angular span which is a substantial fraction of a quadrant of its associated inner-rim formation.

10. As an article of manufacture, a single unitary flexibly compliant mounting-adapter element having capability of assembly to another such mounting-adapter element for iris-stabilized mounting of an intra-ocular lens element of circular peripheral contour, comprising a circumferentially continuous centrally open inner-rim body formation of inner diameter less than the outer diameter of the lens element and for axial-retaining abutment with one axial side of the rim of the lens element, a pair of lens-positioning feet integral with diametrically opposed quadrant regions of said body formation and radially outwardly extending therefrom, and foot-engaging means integrally formed with opposed remaining quadrant regions of said body formation, each said foot-engaging means being at a radius greater than such lens-element outer radius and including means having interlocking engagement with one lens-positioning foot of another such mounting-adapter element when the latter is assembled to the other axial side of the lens element and when lens-positioning feet of the two such mounting-adapter elements are in quadrant-staggered interlace.

11. The article of claim 10, in which each said foot-engaging means comprises an arcuate tab having a foot-receiving locating slot at a radius which is at least as great as the outer radius of the lens element.

12. The article of claim 11, in which the angular margin of each lens-positioning foot is undercut at the radius of tab-slot locking engagement and in which the effective angular width of each lens-positioning foot is such as to produce detent interference with the angular margins of each said slot upon foot-to-slot assembly of two such mounting-element adapters to opposite axial sides of the periphery of lens element.

13. The article of claim 10, in which each of said lens-positioning feet comprises a radially outwardly bowed strip integrally formed at its ends with angularly spaced regions of the associated quadrant of said body formation, thereby defining a tool-receiving opening between each strip and its associated body quadrant.

14. The article of claim 10, in which each of said lens-positioning feet comprises a nominally flat radially outward tab having an aperture for reception of a manipulative tool.

15. In combination, a hypodermic needle, and an intra-ocular lens-and-mount assembly pre-assembled to said needle, the mount of said assembly including flexibly compliant apertured iris-stabilizing feet projecting radially outward of generally diametrically opposed regions of said lens-and-mount assembly, said feet being resiliently bent to one axial side of said assembly, and said needle passing through an aperture of each of said feet and generally diametrically across said axial side of said assembly.

16. The combination of claim 15, in which said needle is characterized by an elongate characterized surface having angularly keyed engagement with diametrically opposed regions of the pre-assembled lens mount.

17. The combination of claim 16, in which said needle is the discharge orifice of a syringe, and in which said elongate characterized surface is flat and is one of two generally in a diametral plane of said needle, whereby syringe-discharged liquid is initially directed at flat-region engagement with said pre-assembled lens and mount.

18. The tool of claim 16, in which said characterized surface extends from a limited shoulder to the needle end for a distance which slightly exceeds the diametral span between apertures of said lens-positioning feet, whereby longitudinal manipulative stability of the pre-assembled lens and mount is enhanced during operative insertion at the iris-opening.

19. The method of operatively installing a pre-assembled intra-ocular lens and its mount at an iris opening, such mount having diametrically opposed and apertured resiliently compliant radially projecting lens-positioning feet to be stabilized by and behind the iris, each of said feet having an aperture for manipulative-tool engagement, which method comprises selecting a saline-solution syringe having a hypodermic-needle discharge orifice, assembling the pre-assembled lens and mount to the hypodermic needle with the needle passing transverse to the lens axis by transiently resiliently deforming said feet to permit needle insertion on a diametrical alignment through both apertures, manipulating the pre-assembly via the syringe so as to place first one and then the other deformed foot behind the iris, removing the needle from the iris-engaged pre-assembly, and discharging syringe solution to fill the eye cavity during at least a part of such manipulation.

20. In combination, a manipulable tool having an elongate end along which an intra-ocular lens-and-mount assembly is pre-assembled, the mount of said assembly including flexibly compliant apertured iris-stabilizing feet projecting radially outward of generally diametrically opposed regions of said lens-and-mount assembly, said feet being resiliently bent to one side of said assembly, and said elongate end passing through an aperture of each of said feet and generally diametrically across said axial side of said assembly and retaining the resiliently bent condition of said feet, whereby insertion of said feet via an iris opening is facilitated by the thus-retained condition of said feet, and whereby longitudinal removal of said elongate end by retraction from said apertures will allow the resilient compliance of said feet to assume a more radially outwardly directed and iris-stabilized position.

21. An intra-ocular lens-implant kit, comprising a package containing an intra-ocular lens and mount in assembled relation, said mount including flexibly compliant apertured iris-stabilizing feet projecting radially outward of generally diametrically opposed regions of said assembled lens and mount, and a disposable mount-engageable manipulable tool having an elongate end of sufficient length and reduced section as to be retractably enterable in generally diametrically aligned apertures of said feet when said feet are resiliently bent to one axial side of said assembled lens and mount.

22. The kit of claim 21, in which said tool is a hypodermic needle.

23. The kit of claim 21, in which said needle is pre-assembled to said assembled lens and mount via the generally diametrically aligned apertures of said resiliently bent feet.

24. As an article of manufacture, a single unitary mounting-adapter element having capability of assembly to an optically finished intra-ocular lens element of circular peripheral contour, comprising a blank formed from relatively thin flexibly compliant sheet plastic material, said blank comprising a circumferentially continuous centrally open body in substantial conformance with and for generally registering adjacency to the periphery of the lens element, the contour of the central opening of said body being characterized by at least four angularly spaced tabs separated by cutaway regions extending at least to the locus of the lens-periphery diameter, and at least four iris-stabilizing lens-positioning feet extending radially outwardly of said body at angularly spaced locations.

25. The article of claim 24, in which at least two of said feet are apertured and at generally diametrically opposed locations.

26. The article of claim 24, in which said tabs and feet are at quadrant spacing.

27. The article of claim 24, in which said tabs are of substantially quadrant extent, and in which at least one of said feet is in each tab quadrant.

28. The article of claim 27, in which the feet in one pair of diametrically opposed quadrants is larger than the single foot in each of the remaining quadrants.

29. The article of claim 28, in which said single feet are apertured for manipulative-tool engagement.

30. The combination of claim 15, in which said needle is characterized by an elongate key-characterized surface having angularly keyed engagement with at least one of two diametrically opposed regions of the pre-assembled lens and mount, and in which said needle is further characterized by a lens-mount-interfering stop formation for limiting the longitudinal extent of needle insertion via said lens-positioning feet.

31. The article of claim 13, in which the contour of at least one of said tool-receiving openings includes a key-action formation having key engagement with a key formation of an inserted tool.

32. The article of claim 13, in which the inner contour of at least one of said tool-receiving openings includes an edge which extends chordally with respect to the bow of the associated bowed strip.

* * * * *